United States Patent
Pintel et al.

(10) Patent No.: US 9,078,617 B2
(45) Date of Patent: Jul. 14, 2015

(54) APPARATUS FOR NON-INVASIVE OPTICAL MONITORING

(75) Inventors: Ofer Pintel, Matan (IL); Michael Bendkowski, Jerusalem (IL); Ilan Breskin, Tel-Aviv (IL); Yaakov Metzger, Hod Hasharon (IL); Revital Pery Shechter, Rishon Lezion (IL)

(73) Assignee: OR-NIM MEDICAL LTD., Lod (IL)

( * ) Notice: Subject to any disclaimer, the term of this patent is extended or adjusted under 35 U.S.C. 154(b) by 1082 days.

(21) Appl. No.: 12/402,582

(22) Filed: Mar. 12, 2009

(65) Prior Publication Data

US 2009/0234228 A1   Sep. 17, 2009

Related U.S. Application Data

(60) Provisional application No. 61/037,029, filed on Mar. 17, 2008.

(51) Int. Cl.
*A61B 5/00* (2006.01)
*A61B 8/00* (2006.01)
*A61B 5/1455* (2006.01)

(52) U.S. Cl.
CPC .............. *A61B 8/42* (2013.01); *A61B 5/0097* (2013.01); *A61B 5/14552* (2013.01); *A61B 5/6843* (2013.01); *A61B 8/4236* (2013.01); *A61B 8/4281* (2013.01); *A61B 8/4438* (2013.01); *A61B 8/4472* (2013.01); *A61B 2562/08* (2013.01)

(58) Field of Classification Search
None
See application file for complete search history.

(56) References Cited

U.S. PATENT DOCUMENTS

| | | | |
|---|---|---|---|
| 3,435,228 A | 3/1969 | Gordon | |
| 4,059,010 A | 11/1977 | Sachs | |
| 4,611,288 A * | 9/1986 | Duret et al. | 700/163 |
| 4,669,465 A * | 6/1987 | Moore et al. | 606/7 |
| 4,672,969 A * | 6/1987 | Dew | 607/89 |
| 4,854,320 A * | 8/1989 | Dew et al. | 606/3 |
| 5,002,051 A * | 3/1991 | Dew et al. | 607/89 |
| 5,140,984 A * | 8/1992 | Dew et al. | 607/89 |
| 5,152,293 A | 10/1992 | Vonesh et al. | |
| 5,199,431 A * | 4/1993 | Kittrell et al. | 600/477 |
| 5,299,570 A | 4/1994 | Hatschek | |
| 5,348,002 A * | 9/1994 | Caro | 600/310 |

(Continued)

FOREIGN PATENT DOCUMENTS

| | | |
|---|---|---|
| EP | 1810610 A1 | 7/2007 |
| WO | 02/17779 A1 | 3/2002 |

(Continued)

OTHER PUBLICATIONS

Invitation to Pay Additional Fees, mailed Aug. 20, 2009, from corresponding International Application No. PCT/IL2009/000287, filed Mar. 12, 2009.

*Primary Examiner* — Nicholas Evoy
(74) *Attorney, Agent, or Firm* — Browdy and Neimark, PLLC

(57) ABSTRACT

A probe assembly is presented for use in monitoring one or more parameters of a subject. The probe assembly comprises: an acoustic port for transmitting acoustic radiation into a region of interest in the subject, at least one light output port for transmitting incident light towards the region of interest, at least one light input port for receiving light returned from the subject, and a control utility integrated in the probe assembly, said control utility being configured for controlling at least one condition of a monitoring procedure and enabling the monitoring procedure upon detecting that said at least one condition is satisfied.

25 Claims, 9 Drawing Sheets

(56) References Cited

U.S. PATENT DOCUMENTS

| | | | |
|---|---|---|---|
| 5,348,003 A * | 9/1994 | Caro | 600/310 |
| 5,779,631 A * | 7/1998 | Chance | 600/328 |
| 5,781,294 A * | 7/1998 | Nakata et al. | 356/487 |
| 5,799,656 A * | 9/1998 | Alfano et al. | 600/473 |
| 5,840,023 A * | 11/1998 | Oraevsky et al. | 600/407 |
| 5,999,836 A * | 12/1999 | Nelson et al. | 600/407 |
| 6,047,602 A | 4/2000 | Lynnworth | |
| 6,120,460 A * | 9/2000 | Abreu | 600/558 |
| 6,123,668 A * | 9/2000 | Abreu | 600/405 |
| 6,213,943 B1 * | 4/2001 | Abreu | 600/405 |
| 6,312,393 B1 * | 11/2001 | Abreu | 600/558 |
| 6,405,069 B1 * | 6/2002 | Oraevsky et al. | 600/407 |
| 6,423,001 B1 * | 7/2002 | Abreu | 600/405 |
| 6,456,862 B2 | 9/2002 | Benni | |
| 6,466,806 B1 * | 10/2002 | Geva et al. | 600/310 |
| 6,498,942 B1 | 12/2002 | Esenaliev et al. | |
| 6,571,118 B1 * | 5/2003 | Utzinger et al. | 600/476 |
| 6,590,830 B1 | 7/2003 | Garlick et al. | |
| 6,652,459 B2 * | 11/2003 | Payne et al. | 600/439 |
| 6,815,694 B2 * | 11/2004 | Sfez et al. | 250/492.1 |
| 6,826,422 B1 * | 11/2004 | Modell et al. | 600/407 |
| 6,847,490 B1 * | 1/2005 | Modell et al. | 359/642 |
| 6,944,322 B2 * | 9/2005 | Johnson et al. | 382/128 |
| 7,048,687 B1 | 5/2006 | Reuss et al. | |
| 7,049,622 B1 | 5/2006 | Weiss | |
| 7,403,805 B2 * | 7/2008 | Abreu | 600/318 |
| 7,500,953 B2 * | 3/2009 | Oraevsky et al. | 600/458 |
| 7,654,957 B2 * | 2/2010 | Abreu | 600/399 |
| 7,777,891 B2 * | 8/2010 | Hasegawa | 356/485 |
| 7,914,442 B1 * | 3/2011 | Gazdzinski | 600/109 |
| 7,967,016 B2 * | 6/2011 | Anderson et al. | 128/898 |
| 8,214,010 B2 * | 7/2012 | Courtney et al. | 600/407 |
| 8,275,442 B2 * | 9/2012 | Allison | 600/407 |
| 8,401,618 B2 * | 3/2013 | Lorenzo et al. | 600/425 |
| 8,423,116 B2 * | 4/2013 | Balberg et al. | 600/407 |
| 8,636,648 B2 * | 1/2014 | Gazdzinski | 600/109 |
| 8,636,649 B1 * | 1/2014 | Gazdzinski | 600/109 |
| 8,686,335 B2 * | 4/2014 | Schmid et al. | 250/205 |
| 8,812,088 B2 * | 8/2014 | Ripoll Lorenzo et al. | 600/476 |
| 8,839,672 B2 * | 9/2014 | Emelianov et al. | 73/606 |
| 2002/0017141 A1 | 2/2002 | Satoh | |
| 2002/0049374 A1 * | 4/2002 | Abreu | 600/405 |
| 2002/0049389 A1 * | 4/2002 | Abreu | 600/558 |
| 2002/0097374 A1 * | 7/2002 | Payne et al. | 351/200 |
| 2002/0161290 A1 * | 10/2002 | Chance | 600/323 |
| 2003/0069489 A1 * | 4/2003 | Abreu | 600/405 |
| 2003/0139687 A1 * | 7/2003 | Abreu | 600/558 |
| 2004/0030325 A1 * | 2/2004 | Cahir et al. | 606/9 |
| 2004/0127782 A1 | 7/2004 | Sfez et al. | |
| 2004/0267335 A1 * | 12/2004 | Tulip et al. | 607/89 |
| 2005/0020926 A1 * | 1/2005 | Wiklof et al. | 600/476 |
| 2005/0038344 A1 | 2/2005 | Chance | |
| 2005/0113656 A1 * | 5/2005 | Chance | 600/323 |
| 2005/0113698 A1 * | 5/2005 | Kristoffersen et al. | 600/459 |
| 2005/0215901 A1 * | 9/2005 | Anderson et al. | 600/445 |
| 2005/0234319 A1 * | 10/2005 | Mandelis et al. | 600/407 |
| 2006/0004306 A1 * | 1/2006 | Altshuler et al. | 601/3 |
| 2006/0020309 A1 * | 1/2006 | Altshuler et al. | 607/88 |
| 2006/0058683 A1 * | 3/2006 | Chance | 600/476 |
| 2006/0058685 A1 * | 3/2006 | Fomitchov et al. | 600/476 |
| 2006/0122475 A1 * | 6/2006 | Balberg et al. | 600/323 |
| 2006/0184042 A1 * | 8/2006 | Wang et al. | 600/476 |
| 2006/0247506 A1 * | 11/2006 | Balberg et al. | 600/323 |
| 2006/0259022 A1 * | 11/2006 | Lin | 606/4 |
| 2006/0282136 A1 * | 12/2006 | Tulip et al. | 607/89 |
| 2006/0282137 A1 * | 12/2006 | Nightingale et al. | 607/90 |
| 2007/0038206 A1 * | 2/2007 | Altshuler et al. | 606/20 |
| 2007/0043341 A1 * | 2/2007 | Anderson et al. | 606/12 |
| 2007/0142718 A1 * | 6/2007 | Abreu | 600/323 |
| 2007/0198004 A1 * | 8/2007 | Altshuler et al. | 606/9 |
| 2007/0232940 A1 * | 10/2007 | Fine et al. | 600/504 |
| 2008/0058783 A1 * | 3/2008 | Altshuler et al. | 606/9 |
| 2008/0091187 A1 * | 4/2008 | Ferren et al. | 606/36 |
| 2008/0123083 A1 * | 5/2008 | Wang et al. | 356/73 |
| 2008/0132886 A1 * | 6/2008 | Cohen et al. | 606/34 |
| 2008/0154128 A1 * | 6/2008 | Milner | 600/427 |
| 2008/0172047 A1 * | 7/2008 | Altshuler et al. | 606/9 |
| 2008/0177139 A1 * | 7/2008 | Courtney et al. | 600/109 |
| 2008/0183162 A1 * | 7/2008 | Altshuler et al. | 606/9 |
| 2008/0214988 A1 * | 9/2008 | Altshuler et al. | 604/21 |
| 2008/0259422 A1 * | 10/2008 | Lin | 359/196 |
| 2008/0281306 A1 * | 11/2008 | Lin | 606/10 |
| 2009/0036761 A1 * | 2/2009 | Abreu | 600/318 |
| 2009/0054908 A1 * | 2/2009 | Zand et al. | 606/130 |
| 2009/0069674 A1 * | 3/2009 | Masumura et al. | 600/425 |
| 2009/0069685 A1 * | 3/2009 | Nishihara et al. | 600/443 |
| 2009/0069871 A1 * | 3/2009 | Mahadevan-Jansen et al. | 607/89 |
| 2009/0073453 A1 * | 3/2009 | Hasegawa | 356/477 |
| 2009/0105588 A1 * | 4/2009 | Emelianov et al. | 600/438 |
| 2009/0118622 A1 * | 5/2009 | Durkin et al. | 600/473 |
| 2009/0149761 A1 * | 6/2009 | Zou et al. | 600/476 |
| 2009/0240310 A1 * | 9/2009 | Kennedy | 607/89 |
| 2009/0326523 A1 * | 12/2009 | Lazarev et al. | 606/9 |
| 2010/0010325 A1 * | 1/2010 | Ridder et al. | 600/310 |
| 2010/0036209 A1 * | 2/2010 | Ferren et al. | 600/301 |
| 2010/0145180 A1 * | 6/2010 | Abreu | 600/399 |
| 2010/0160790 A1 * | 6/2010 | Ibok | 600/476 |
| 2010/0245766 A1 * | 9/2010 | Zhang et al. | 351/206 |
| 2011/0021924 A1 * | 1/2011 | Sethuraman et al. | 600/463 |
| 2011/0071402 A1 * | 3/2011 | Masumura | 600/476 |
| 2011/0125004 A1 * | 5/2011 | Thumma et al. | 600/407 |
| 2011/0303015 A1 * | 12/2011 | Ichihara et al. | 73/656 |
| 2012/0283709 A1 * | 11/2012 | Reichert et al. | 606/9 |
| 2012/0283710 A1 * | 11/2012 | Liu et al. | 606/9 |
| 2012/0283711 A1 * | 11/2012 | Liu et al. | 606/9 |
| 2012/0283712 A1 * | 11/2012 | Youngquist et al. | 606/9 |
| 2012/0283803 A1 * | 11/2012 | Liu et al. | 607/89 |
| 2012/0289948 A1 * | 11/2012 | Youngquist | 606/9 |
| 2013/0030423 A1 * | 1/2013 | Reichert et al. | 606/9 |
| 2013/0109950 A1 * | 5/2013 | Herzog et al. | 600/407 |
| 2013/0116538 A1 * | 5/2013 | Herzog et al. | 600/407 |
| 2013/0168532 A1 * | 7/2013 | Schmid et al. | 250/205 |
| 2013/0281819 A1 * | 10/2013 | Schmid | 600/407 |
| 2013/0296683 A1 * | 11/2013 | Herzog et al. | 600/407 |
| 2013/0296684 A1 * | 11/2013 | Miller et al. | 600/407 |
| 2013/0296701 A1 * | 11/2013 | Zalev et al. | 600/440 |
| 2013/0303875 A1 * | 11/2013 | Joy et al. | 600/407 |
| 2013/0304405 A1 * | 11/2013 | Schmid et al. | 702/56 |
| 2013/0335441 A1 * | 12/2013 | Zalev et al. | 345/629 |
| 2013/0338475 A1 * | 12/2013 | Herzog et al. | 600/407 |
| 2013/0338501 A1 * | 12/2013 | Clingman | 600/440 |
| 2014/0005544 A1 * | 1/2014 | Zalev et al. | 600/440 |
| 2014/0012124 A1 * | 1/2014 | Zalev | 600/407 |
| 2014/0012135 A1 * | 1/2014 | Freeman et al. | 600/473 |
| 2014/0012140 A1 * | 1/2014 | Freeman et al. | 600/476 |
| 2014/0051966 A1 * | 2/2014 | Irisawa | 600/407 |
| 2014/0051967 A1 * | 2/2014 | Irisawa | 600/407 |
| 2014/0194723 A1 * | 7/2014 | Herzog et al. | 600/407 |

FOREIGN PATENT DOCUMENTS

| | | |
|---|---|---|
| WO | 2005/025399 A2 | 3/2005 |
| WO | 2006/097910 A1 | 9/2006 |

* cited by examiner

APPARATUS FOR NON-INVASIVE OPTICAL MONITORING

RELATED APPLICATIONS

This application claims the benefit under 35 USC 119(e) of U.S. Provisional Application No. 61/037,029, filed on Mar. 17, 2008, which is incorporated herein by reference in its entirety.

FIELD OF THE INVENTION

This invention is generally in the field of medical devices, and relates to a probe device and a monitoring system utilizing such a probe device for carrying out measurements on a subject. The invention is particularly useful for monitoring various parameters, e.g. oxygen saturation in blood vessels, capillaries and venules, and oxygen saturation in deep tissues, such as brain, muscle, kidney and other organs.

BACKGROUND OF THE INVENTION

Various techniques of non invasive monitoring of conditions of a subject have been developed. These techniques include impedance-based measurement techniques, photoacoustic measurements, acoustic measurements (Doppler measurements), and optical measurements (e.g. oximetry).

Another approach, based on use of ultrasound tagging of light in measurements of various chemical and physiological parameters, has been developed and disclosed for example in WO 06/097910 and WO 05/025399, both assigned to the assignee of the present application.

SUMMARY OF THE INVENTION

The present invention provides a novel probe assembly and a monitoring device using the same enabling effective continuous monitoring of one or more conditions of a subject.

The present invention takes advantage of the monitoring techniques utilizing principles of ultrasound tagging of light, for example as disclosed in the above-indicated publications WO 05/025399 and WO 06/097910 assigned to the assignee of the present application. Thus, a probe assembly of the invention operates to irradiate a region of interest with acoustic waves while taking optical measurements on said region of interest.

The present invention provides for controlling condition(s) of the monitoring procedure such as to allow the monitoring procedure to start and/or to proceed in case certain condition(s) exist(s). The condition to be controlled may be the existence of a contact between the probe and the subject's tissue and/or a degree of coupling between the subject and an acoustic/light ports at the probe, and/or positioning of the probe in a docking station, etc. If the required condition is not satisfied, the monitoring procedure is not allowed, for example by canceling or disabling the laser emission at all, or disabling the laser emission in the monitoring mode.

Thus, the present invention, according to its one broad aspect, provides a probe assembly for use in monitoring one or more parameters of a subject. The probe assembly comprises an acoustic port for transmitting acoustic radiation into a region of interest in the subject, at least one light output port for transmitting incident light towards the region of interest, at least one light input port for receiving light returned from the subject, and a control utility integrated in the probe assembly. The control utility is configured for controlling at least one condition of a monitoring procedure and for enabling the monitoring procedure upon identifying that said at least one condition is satisfied.

In some embodiments of the invention, the control utility comprises at least one of the following:
(i) a coding chip adapted for identifying whether the probe assembly is a certified one; and
(ii) a sensor and actuator system adapted for sensing a predetermined condition of the probe assembly.

Preferably, the control utility comprises a memory unit adapted for recording data indicative of measurements taken on a specific subject during a certain period of time. In some embodiments of the invention, these data serve as a measurement history of the specific subject. The data recorded in the control utility of certain probe assembly may include data portions corresponding to measurements taken on said subject by one or more different probe assemblies.

As indicated above, the control utility may comprise a sensor and actuator system adapted for sensing one or more conditions of the probe assembly. This may be determination of a degree of attachment between the probe assembly and the subject, which in turn is indicative of a degree of coupling between the subject and acoustic and/or light ports.

In some embodiments, the probe assembly is configured as a two-part device comprising a first unit (probe body unit) and a second unit. The latter presents an interface between the probe assembly and the subject when the probe assembly is put in operation, and may be configured so that it can be removed from, or connected to the first unit. The second unit may carry at least a part of the control utility. For example, the second unit carries a memory unit adapted for recording data indicative of measurements taken on a specific subject during a certain period of time. The recorded data may be used as a measurement history of the specific subject, and may for example include data portions corresponding to the measurements taken on the same subject by at least two different probe assemblies.

The first probe body unit may comprise the acoustic port, the at least one light output port, and the at least one light input port. The second unit thus interfaces an output surface of the first unit through which acoustic and light radiations are transmitted in between the probe assembly and the subject, and may transmit acoustic and light radiation therethrough towards and from the subject.

The second unit may be configured as a flexible cover on an output surface of the first unit.

The probe assembly may comprise an ultrasound-skin coupling pad. The latter comprises one or more materials selected to provide desired acoustic coupling between the acoustic port and the subject (e.g. has acoustic impedance similar to that of tissue or skin of the subject).

In some embodiments relating to the two-part design of the probe assembly, the second unit is configured as a probe-subject adhesive assembly unit being associated with a probe-subject adhesive media, e.g. including such probe-subject adhesive media. The probe-subject adhesive media may comprise the ultrasound-skin coupling pad providing the desired acoustic coupling being substantially transparent for a wavelength range used in the probe.

The ultrasound-skin coupling pad is preferably electrically insulating. The ultrasound-skin coupling pad may have a matrix that is a polymerization product of a suspension of elastomeric resins in a plasticizer. Such ultrasound-skin coupling pad may comprise Polymelt™.

In yet another aspect of the invention there is provided a monitoring system for monitoring one or more parameters of a subject. The system comprises one or more of the above-described probe assemblies. The control utility is configured and operable to carry out at least one of the following: (i) recording data indicative of measurements taken on a specific subject during a certain period of time; (ii) identifying whether the probe assembly is a certified one; and (iii) sensing at least one condition of the monitoring system and enabling operation upon identifying that said at least one condition is satisfied.

In multiple-probe embodiments of the monitoring system, the memory unit of each of the probe assemblies is preferably adapted for storing data indicative of results of measurements taken by all the probes (or at least some of them).

According to yet another aspect of the invention there is provided a probe assembly for use in monitoring one or more parameters of a subject. The probe assembly comprises: an acoustic port for transmitting acoustic radiation into a region of interest in the subject; and an ultrasound-skin coupling pad presenting an interface between the subject's surface and the acoustic port, the ultrasound-skin coupling pad comprising a matrix that is a polymerization product of a suspension of elastomeric resins in a plasticizer.

The ultrasound-skin coupling pad may be substantially transparent to light of a predetermined wavelength range and is preferably electrically insulating.

According to yet another aspect of the invention there is provided an acoustic coupling device for placing on a subject body surface to interface between the body surface and an acoustic unit, the acoustic coupling device comprising a matrix that is a polymerization product of a suspension of elastomeric resins in a plasticizer.

The acoustic coupling pad has a sticky surface to permit tight contact with a body surface substantially without air pockets.

The invention also provides a device configured as a cover for mounting on an outer surface of an acoustic probe by which the probe is brought in contact with a subject when in operation, said cover comprising a matrix that is a polymerization product of a suspension of elastomeric resins in a plasticizer.

The probe assembly can be configured as a two-part device comprising a first probe body unit and a second unit (e.g. probe-subject adhesive assembly). The second unit presents an interface between the first probe body unit and the subject when the probe assembly is put in operation. The second unit may be removed from or connected to the first probe body unit.

In some embodiments, the second unit carries at least a part of the control utility. Preferably, the second unit carries the memory unit adapted for recording data indicative of measurements taken on a specific subject during a certain period of time.

The second unit may be associated with a probe-subject adhesive media. For example, the second unit comprises such a probe-subject adhesive media.

In some embodiments of the invention, the first probe body unit comprises the acoustic port, the at least one light output port, and the at least one light input port. The second unit interfaces between the probe body and the subject on an output surface of the probe body unit through which acoustic and light radiations are transmitted.

The second unit may be configured as a flexible cover on an output surface of the first probe body unit.

In the two-part design of the probe assembly, an ultrasound-skin coupling pad if used is located in the second unit. As indicated above, the ultrasound-skin coupling pad may be substantially transparent for a wavelength range used in the probe. The ultrasound-skin coupling pad has acoustic impedance similar to that of tissue or skin of a subject. For example, the ultrasound-skin coupling pad includes a matrix that is a polymerization product of a suspension of elastomeric resins in a plasticizer. For example, the ultrasound-skin coupling pad comprises Polymelt. Preferably, the ultrasound-skin coupling pad is electrically insulating.

According to yet another aspect of the invention, there is provided a probe assembly for use in monitoring one or more parameters of a subject, the probe assembly being configured as a two-part device comprising a probe-subject adhesive assembly unit and a probe body unit, wherein:

the first unit is configured as a probe body unit and comprises an acoustic port for transmitting acoustic radiation into a region of interest in the subject, at least one light output port for transmitting incident light towards the region of interest, at least one light input port for receiving light returned from the subject, the second unit presents an interface between the first unit and the subject when the probe assembly is put in operation and comprises an electronic unit having a memory utility adapted for recording data indicative of measurements taken on a specific subject during a certain period of time, enabling use of said data as a measurement history of the specific subject, the recorded data corresponding to the measurements being taken by one or more of the probe assemblies.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 4A shows the microswitch sensor in its closed state, and FIG. 4B shows the microswitch sensor in its normally open state;

FIG. 5A shows the probe-tissue relative position such that the reflected light beam reaches the detector of the proximity sensor and FIG. 5B shows the probe-tissue relative position in which the reflected light beam does not reach the detector;

DETAILED DESCRIPTION OF THE PREFERRED EMBODIMENTS

Figure 1:
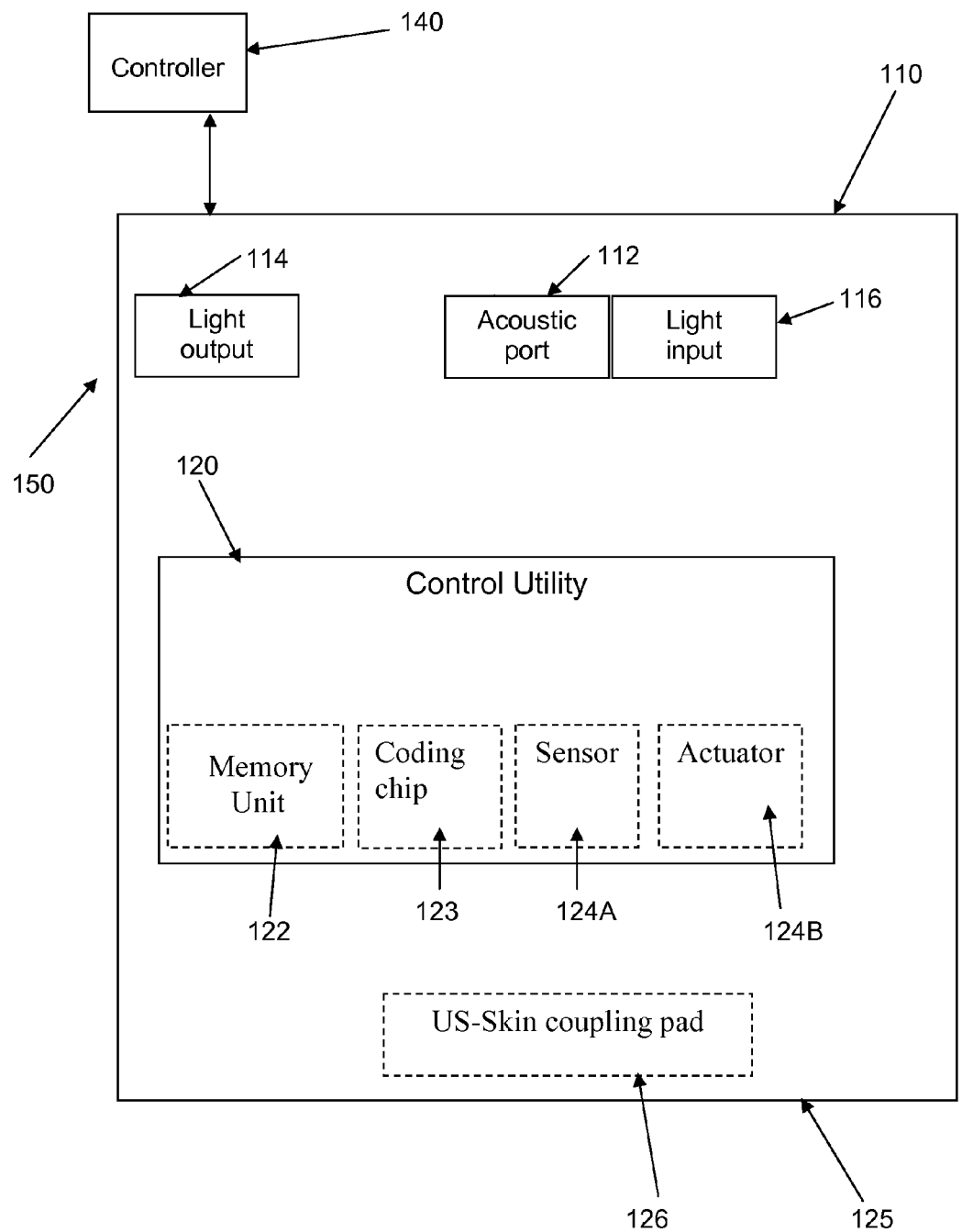
FIG. 1 is a block diagram of an example of a probe assembly according to the invention.

Referring to FIG. 1, there is illustrated, by way of a block diagram, an example of a probe assembly, generally designated 110, which is configured and operable according to the invention for monitoring one or more parameters of a subject. The probe assembly 110 is adapted for carrying out ultrasound tagging based optical measurements. The principles of such a technique are described for example in wo 2006/097910 and wo 2005/025399, both assigned to the assignee of the present application.

Probe assembly 110 includes an acoustic port 112 for transmitting acoustic radiation into a region of interest in the subject, at least one light output port 114 for transmitting incident light towards the region of interest, and at least one light input port 116 for receiving light returned from the subject. These ports are typically located on a common housing or support structure (not shown here).

It should be understood that the acoustic port may be constituted by an acoustic transducer itself or by an acoustic guide. Similarly, the light output port may be a light source itself (light emitter) or may be connectable to an external light source via an appropriate light guide (an optical fiber or an optical fiber bundle); and the light input port may be that of an on-probe photodetection system or may be connectable to an off-probe photodetector via a light guide. There could be more than one ingoing light guide, as well as more than one outgoing light guide.

Typically, the probe assembly itself includes the light ports, while light emitter(s) (e.g. laser(s)), as well as light detector(s), are located outside the probe assembly and are connectable to the respective ports via light guides (optical fibers or optical fiber bundles). For example, a fiber, at its one end (e.g. the end which is intended for connection with the probe) is equipped with a connector (21 in FIG. 9B), e.g. a clip-bridge, for example such as disclosed in U.S. Pat. No. 6,188,825. Such a connector is configured to ensure a normally-closed state of the fiber end of the probe (i.e. state in which no light transmission is allowed through the end of the fiber). The state of this connector changes into an open state (i.e. light transmission is allowed) only upon connection to the respective light port at the controller. A corresponding adapter at the controller side is also normally closed, to prevent dust collection, and opens upon connection to the above-described optical connector at the probe side (i.e. both sides are normally closed, and become open only upon connection to one another).

As further illustrated in a specific but non-limiting example of FIG. 1, the probe assembly 110 communicates with a controller 140, which typically includes a computer system. The communication between the probe assembly and the controller may be via wires or by means of wireless signal/data transmission (e.g. RF, IR, acoustic). The controller 140 may include among other things a light source system and/or a detection system and/or an acoustic generator (e.g. arbitrary waveform generator).

Preferably, a light guide connecting an external light emitter (e.g. in the controller) and a light output port at the probe is a small core fiber (e.g. a single-mode, a 50 μm or a 62.5 μm core fiber). As for a light guide connecting an external light detector (e.g. in the controller) and a corresponding light input port at the probe, it has an appropriate cross-sectional dimension of the core in order to satisfy the collection efficiency requirement. For example, a fiber or a fiber bundle, having a core of a diameter equal to or higher than 100 μm can be used. The maximal diameter and numerical aperture of a collecting fiber is determined so that the total path difference between light traveling in different paths in the fiber core is less than the coherence length of the light source.

According to the invention, the probe device 110 also includes an integral control utility 120. Generally, the control utility allows for identifying whether the probe assembly is a certified one; and/or is capable of sensing a predetermined condition of the probe assembly (e.g. including a degree of coupling between the subject and the acoustic/light ports); and/or is configured to actuate/operate the measurement of the monitoring unit 150 and/or laser emission; and/or is adapted for recording data indicative of measurements taken on a specific subject during a certain period of time (thus enabling use of this data as a measurement history of the specific subject).

Thus, as shown in FIG. 1, according to some embodiments of the invention, the control utility includes a memory unit 122 (shown in dashed lines in FIG. 1) adapted for recording data indicative of measurements taken on a specific subject during a certain period of time. Such data may serve as a measurement history of a specific subject. Alternatively or additionally, the control utility contains a coding chip 123 for the purpose of controlling the use of a "certified" probe, by using a unique activation code, so that when a probe is attached to the controller 140 only a certified probe could be used. Alternatively or additionally, the control utility 120 includes a sensor 124A (also shown in dashed lines) adapted for sensing one or more predetermined probe condition(s) at which the probe and controller 140 are allowed to operate, and an actuator 124B adapted for enabling/disabling measurement of the monitoring system 150, and/or operation of the controller 140, and/or laser emission, and/or acoustic emission according to sensor identification of these predetermined condition(s).

It should be noted that for performing measurements involving ultrasound tagging of light, a sufficient degree of acoustic coupling between the acoustic port 112 and the subject should be obtained. According to some embodiments of the present invention, the outer surface 125 of the probe assembly 110 by which it is brought into contact with the subject to be monitored, provides the desired acoustic coupling by means of an ultrasound-skin-coupling pad 126. The ultrasound-skin coupling pad could be separate from the transducer or the probe assembly, or it could be an integral part of one or both of these.

Figure 2:
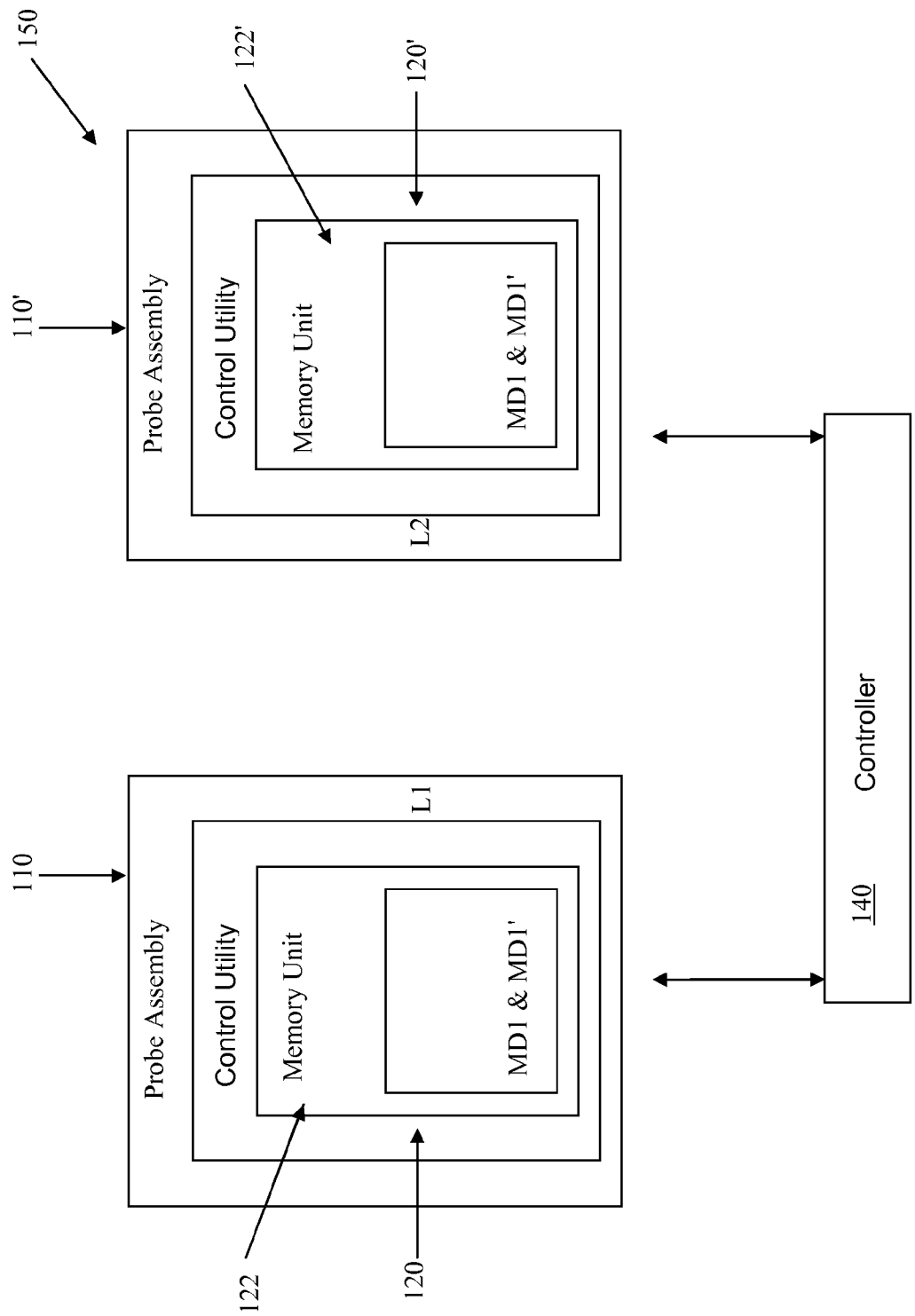
FIG. 2 is a block diagram of an example of a monitoring system of the present invention utilizing multiple probe assemblies of FIG. 1.

In reference to FIG. 2, a monitoring system 150 is exemplified, including a controller 140 and one or more probe assemblies 110. As illustrated in the specific non-limiting example of FIG. 2, the monitoring system includes two probe assemblies 110 and 110' for placing on different locations L1 and L2 on the subject and associated with the same or different regions of interest in the subject. The probe assemblies 110 and 110' are configured as described above with reference to FIG. 1, including their own control utilities 120 and 120'. In the present example, the control utilities include memory units 122 and 122', respectively. It should be understood, although not specifically shown, that the control utility may include the sensor and actuator as well (124A and 124B in FIG. 1). The system configuration is such that each of measurement data pieces MD1 and MD1' corresponding to measurements taken by probe assemblies 110 and 110', or a measurement taken by other probes hooked to the same controller 140, is stored in both memory units 122 and 122'. In addition, the measurement data of a measurement taken by a probe assembly can be transferred to any other probe assembly hooked to any other controller, by connecting them to the same controller, or by connecting all the controllers to another common one. In other words, each of said control utilities is adapted for storing data indicative of results of measurements taken by all or some of the probe assemblies. All the probe assemblies are connectable to the common controller 140, which is configured to determine and synchronize the measurement data and results among all the probe devices. The probe(s) and the controller are configured for appropriate data exchange between them.

The controller 140 may be adapted to control and operate with various data synchronization scenarios. For example, a user may input data indicative of that a "New patient" is to be monitored, in which case the "measurement history" data is deleted from a memory of the controller 140 (the so-called "empty" status). When a user chooses "Continue procedure" mode, the controller 140 operates to transfer/copy most or all of the recently updated stored data from its memory into the memory units (122, 122' in FIG. 2) of all the probes that are connected to it. Similarly, history data may be transferred to the memory of the controller 140 to update the data previously stored therein. In addition, the updated data may be refreshed from time to time between the two (or more) probes. When one of the probe assemblies with a memory unit therein or a part of one of the probe assemblies that includes the memory unit, are replaced by a new one, while the other probe assemblies remain unchanged and retain their memory units, the history data from the memory units of the remaining probe assemblies is transferred to the new memory unit. In an additional example of a data synchronization scenario, the controller is configured to identify a used memory unit. If a new patient is declared, while the memory unit was not changed, the measurement will be disabled until the replacement of the memory unit.

In cases where the operation of the controller or the probe assembly should be controlled automatically, without active involvement of the operator, for example in cases where the monitoring system utilizes laser emission, safety measures should preferably be taken in order to protect the subject in case of an accidental detachment of the probe assembly from the inspected tissue. The sensor 124A and actuator 124B (shown in FIG. 1) are configured to sense predetermined condition(s) of the system, and to enable/disable measurement of the monitoring system 150, and/or operation of the controller 140, and/or laser emission, and/or acoustic emission.

In one embodiment of the invention, such a condition could be the existence of a contact between the probe assembly and the subject's tissue. It could be defined either as a Boolean YES/NO condition, or as a threshold distance between the probe assembly and the subject's skin, as predetermined by the system. Thus, the sensor 124A and actuator 124B may be configured and operable for generating data indicating the distance of the probe to the subject's skin as compared to a predetermined threshold value. In another embodiment of the invention, such a condition could be the positioning of the probe in a docking station. The actuator system typically controls or communicates with the operation system of the acoustic transducer (at the controller) and/or the light source system to thereby selectively permit (enable or disable) the probe operation depending on whether the predetermined condition(s) is/are satisfied. In a specific although non-limiting example, the sensor 124A and actuator 124B serve to cancel or disable any laser emission if risk of unnecessary exposure to the laser radiation is present. According to the example, there are two possible situations for each probe assembly in which laser operation is allowed: (a) probe is attached to the patient; (b) probe is in the docking position. The actuator will not allow any other probe situation, in which case it will stop laser emission.

Figure 3:
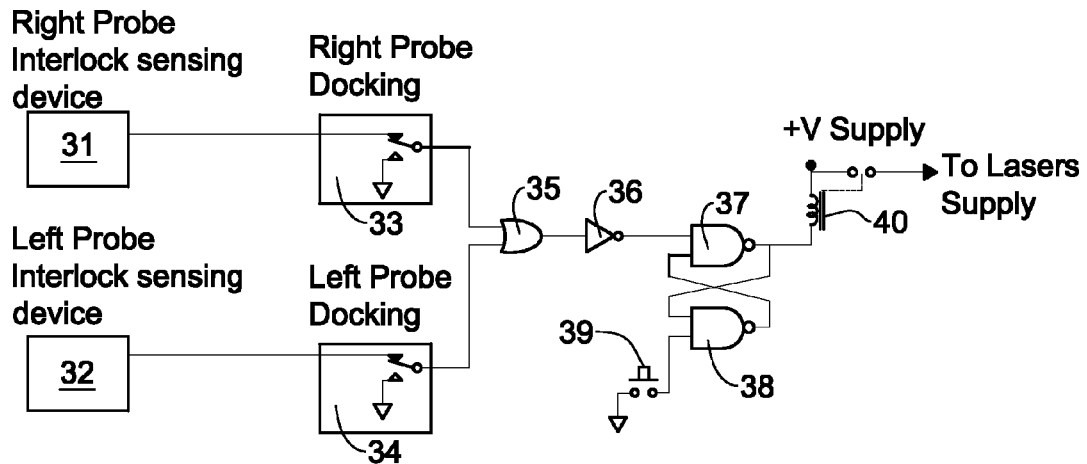
FIG. 3 is an example of a logical circuit for a sensor-actuator ("interlock") system.

In FIG. 3 an example for a logical circuit of such a sensor-actuator ("interlock") system is provided. This specific example is for the case of a monitoring system with two probes. As shown, the probes are equipped with interlock sensing devices 31 and 32 (can be replaced by 124A, 124B and 124A', 124B' of FIG. 1) and docking switches 33 and 34 respectively. In this non-limiting example, the interlock sensors 31, 32 are constituted by a proximity detector. Docking switches 33 and 34 are coupled through a gate 35 to an inverter 36. As an example, a condition is described when one probe assembly (the right one in the figure) is correctly attached to the patient's skin, the proximity detector 31 output is logical "0", and the other probe assembly (the left one in the figure) is in the docking station, the appropriate switch 34 is activated and provides a logical "0" to gate 35. Only when both inputs of gate 35 are logical "0", the output will be logical "0". The output of gate 35 is the input of inverter 36 so that an output of logical "0" at gate 35 results in logical "1" as the output of inverter 36.

A flip-flop set, formed by gates 37 and 38, controls laser emission. Optionally, an additional switch 39 can be used. When switch 39 is activated while the output of inverter 36 is logical "0", the output of gate 38 becomes logical "1", and the output of gate 37 becomes logical "0". This activates a relay 40, thus providing a voltage supply to the lasers.

If for any reason one of the probes becomes detached (generally, its position does not satisfy a predetermined degree of attachment condition, or is released from the docking station during laser operation), gate 35 becomes logical "1", gate 36 becomes logical "0" bringing about logical "1" as the output of gate 37, which in turn releases the relay 40 terminating laser emission. In case of laser emission termination, in order to resume laser operation, switch 39 should be reactivated.

The monitoring system 150 may utilize any one of (but is not limited to) the following sensor 124A and actuator 124B systems to provide such safety measures.

Figure 4A:
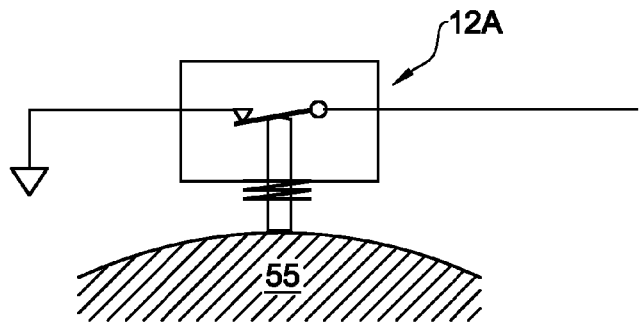
FIGS. 4A and 4B exemplify a sensor-actuator system that incorporates a microswitch sensor, where
Figure 4B:
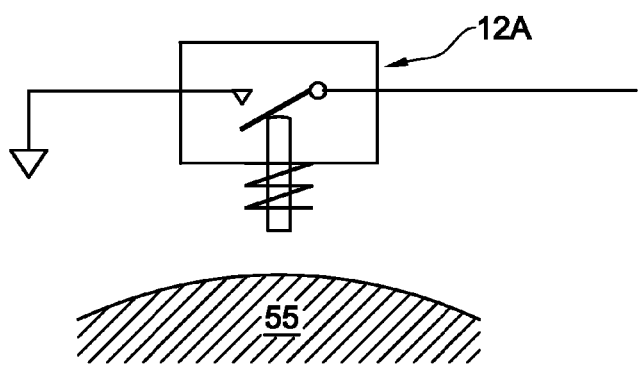

The sensor system may be adapted for direct microswitch sensing, an example of which is given in FIGS. 4A and 4B. A microswitch is located on the probe assembly. The microswitch contacts 12A are normally open (state NO=logic 1), as in FIG. 4B. When the probe assembly is attached to a subject's body, the microswitch is depressed and is thus closed (logical 0), as in FIG. 4A, indicating normal operation. Once the probe assembly is detached from the subject 55, the switch will open the circuit (logical "1") and laser emission and/or operation of the monitoring system will stop, as described above. Examples for micro-switches suited for this embodiment are mechanical micro-switches, with a lever of a few millimeters (see FIGS. 4A and 4B). As a non-limiting example, a microswitch such as ESE-2131 BT of Panasonic, Japan, can be used.

Figure 5A:
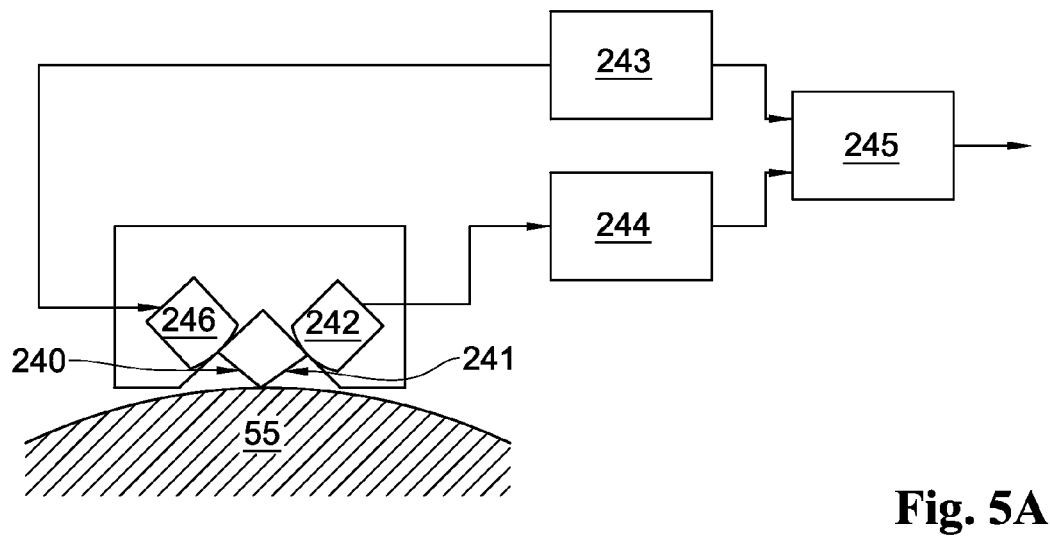
FIGS. 5A and 5B exemplify a sensor-actuator system that incorporates an optical proximity sensor, where
Figure 5B:
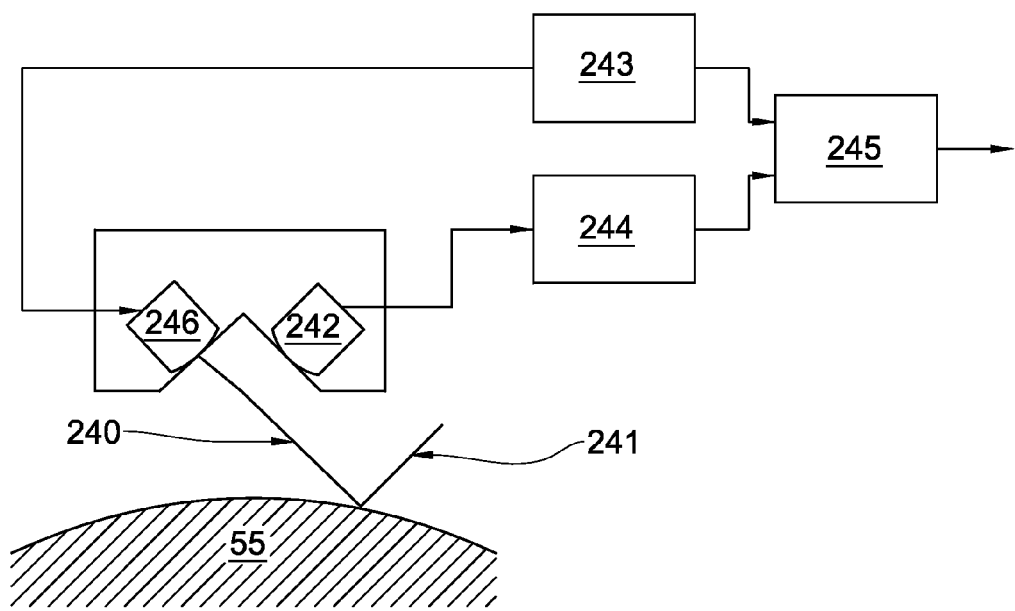

Alternatively or additionally, the sensor system (124A in FIG. 1, or 31, 32 in FIG. 3) may include an optical proximity sensor, an example of which is shown in FIGS. 5A and 5B. In this case a light beam 240 should be directed to the plane of attachment between the probe assembly and the subject body 55, in such a manner that only when proper attachment is achieved the light reflection 241 could be detected in the probe assembly, for example at detector 242 in FIG. 5A, and should be above/below a certain threshold. When the probe is detached the detected signal drops below the threshold (logical "1") and the actuator will disable the operation of the monitoring system and the probe assembly, as in FIG. 5B.

In one embodiment, the reflection of the monitoring system's own laser(s) is detected. In this case, the monitoring system is preferably configured for differentiating between the lasers' and ambient light, by locking the detected light to the modulation between the different lasers, and filtering low-frequency (i.e. ambient) light.

In another embodiment of an optical proximity sensor, an optically coupled IR LED and a detector are utilized. In order to ensure that ambient light does not disturb the operation of this sensor, the LED is modulated and the received signal is correlated with this modulation. In the example shown in FIG. 5A and FIG. 5B, a modulator 243 modulates the transmitted signal from light source 246, while the received signal is transferred from the demodulator 244 to a correlator 245 where it is correlated with the transmitted signal from the modulator 243.

Yet another possible implementation is to use a capacitance proximity sensor adapted for sensing the distance between the probe assembly and the patient's skin by tracking changes in capacitance between the two surfaces. A change in the distance between the two surfaces results in a change in the electric field that brings upon a change in capacitance. There are many methods utilizing this physical phenomenon to measure distance, such as a capacitance bridge, variations in frequency of an oscillator and other devices designed for capacitive proximity detection such as QT113 by Quantum Technology, AD7151 by Analog devices or the like. A capacitance chip, equipped with an electronic circuit capable of determining the capacitance level associated with the probe assembly position relative to the subject's body or a docking site, can be used. Thus, when the capacitance measured exceeds a predetermined capacitance threshold, the output of the circuit is logical "0" (i.e. probe is attached), and when the measured capacitance is below that threshold, the output is logical "1". A more complicated circuitry that detects gradients in capacitance can be utilized, enabling detection of detachment condition demonstrated by a positive gradient in the detected capacitance (logical "1"), relative to steady state (logical "0").

Yet another option is to use ultrasound reflectance detection in the sensor-actuator system. Since the system already includes an acoustic transmitter, the same transmitter can be used, with an acoustic receiver, to detect an ultrasound pulse reflected from the patient's body.

Figure 6:
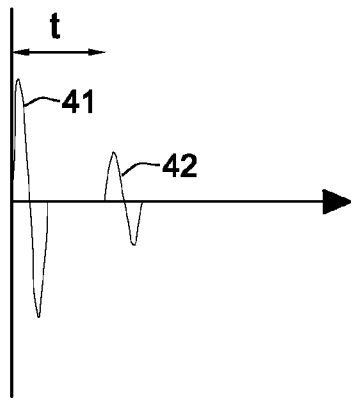
FIG. 6 is an example of an ultrasound pulse and its reflection.

Referring to FIG. 6, an ultrasound pulse 41 is sent from a transducer toward the subject's body, resulting in a reflection 42 of this pulse from the interface with a known feature in the body (such as bone). The reflected pulse 42 is detected in the probe assembly. The time difference between the onset of the sent pulse 41 and the reflected pulse 42 (time delay t) is used to calculate the distance between the probe assembly and the subject's body. A safety threshold for the time delay should be predetermined by the monitoring system, and the operation of the probe assembly and the monitoring system should be controlled accordingly (logical "0" is defined when t is above a predetermined threshold). When the probe assembly is detached from the body and an air gap is established therebetween, the signal is reflected from the edge of the transducer and time delay t is reduced to almost zero, so that the sensor mechanism will thus shut down the operation (logical "1") of the probe/lasers.

Figure 7:
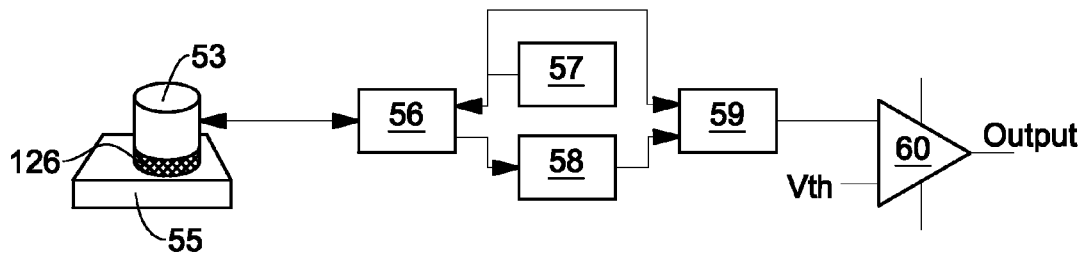
FIG. 7 is an example of a sensor-actuator system that incorporates an ultrasound reflection proximity sensor.

A non-limiting example for a circuit of such a sensor-actuator system is provided in FIG. 7. An acoustic transducer 53 is connected to tissue 55 via an ultrasound-skin coupling pad 126. If the ultrasound-skin coupling pad (as part of the probe assembly) is detached from the subject's tissue, a reflection burst (42 in FIG. 6) will appear at a very short time delay (almost zero) relative to the onset of the pulse. A circuit 56 is the gating mechanism to separate between the transmitted signal and the received one. In order to reduce the chance of a false alarm, the received, reflected, pulse is amplified and delayed in an amplifier 58 and then correlated in an appropriate correlation utility 59 with the transmitted signal 57. The output of the correlation utility 59 is compared with the threshold level, Vth, at a comparator 60, providing an output of logical "0" or logical "1" as the interlock signal.

It should be noted that the probe assembly could be a multi-part unit, e.g. two-part unit, where the components described above could be distributed in between those parts (as will be shown in a specific non-limiting example).

Turning back to FIG. 1, the outer surface 125 of the probe assembly 110 by which it is brought into contact with the subject to be monitored is associated with an acoustic coupling media that provides the desired acoustic coupling between the acoustic port 112 and the subject's skin or tissue, or may include such media as a constructional part thereof. As shown in the figure, the outer surface 125 of the probe assembly includes an ultrasound-skin-coupling pad 126. It is necessary to ensure that the acoustic transducer outer surface/port is in complete contact with the skin, and that no air pockets exist. Due to skin-air impedance mismatch, air pockets reflect acoustic waves and reduce the coupling efficacy of the acoustic waves into the tissue dramatically.

Generally, the probe assembly of the present invention may be used with any suitable ultrasound transmission/coupling material, known in the art (for example gel, hydrogel or a dry coupling pad). However, the gels that are currently in use suffer from a number of drawbacks. For example, most gels are aqueous, therefore over time water evaporates and the gel dries, so that recurrent gel spreading is required. In addition, such gels suffer from their conductive nature, which is undesired in applications where electric insulation between the skin and the apparatus is required. Therefore, there is a need in the art for a dry ultrasound coupling pad. The present invention solves this problem by providing a novel ultrasound-skin coupling pad which is made of a transparent rubber-like elastomer material, which is appropriate for use in any application requiring coupling between any transducer assembly, or any acoustic port, and a subject's tissue or skin.

As a non-limiting example the ultrasound-skin coupling pad could be made of Polymelt which is a suspension of elastomeric resins in a plasticizer. Any other elastomer, with acoustic impedance similar to that of tissue or skin, can be used. The ultrasound-skin coupling pad can be molded in any shape and size.

The ultrasound-skin coupling pad can be used in any application in which coupling is required between a transducer assembly and a subject's skin or tissue. The acoustic properties of the ultrasound-skin coupling pad do not vary with time, so that it is optimal in applications where ultrasound is to be applied for extensive time periods. The pad is electrically insulating, therefore it can be used in applications where electrical insulation is required between the ultrasound transducer and a subject's skin. The ultrasound-skin coupling pad should be able to bear an electric field of approximately 1000 V/mm for it to be insulating.

The ultrasound-skin coupling pad can be used for coupling between any acoustic transducer assembly and any object. Since it can be molded to any shape and size it can fill in air gaps surrounding any measured object that one requires to be coupled to a transducer assembly (provided the object can withstand the temperature of the fluid suspension that is used to create the ultrasound-skin coupling pad). In this manner, the ultrasound-skin coupling pad becomes a buffer for the measured object, and allows the coupling of ultrasound to rough surfaces as well. An example for such an application is NDT (Non Destructive Tests). Such an acoustic coupling pad may be configured as or be a part of a cover mountable onto an outer surface of an acoustic probe (or a probe having acoustic port(s)).

In some embodiments, the acoustic coupling material is substantially transparent for an electromagnetic wavelength range used for illumination by the probe. For example, in applications where ultrasound waves and light are emitted from an overlapping output port, the ultrasound-skin coupling pad medium should be transparent to electromagnetic waves within the emitted wavelength range, to enable the transmittance of light through it. An acoustic coupling pad may include one or more materials possessing transparency/ or opacity to the electromagnetic wavelength range in use.

The ultrasound-skin coupling pad can be biocompatible, and provide direct coupling to the skin, or be covered with a biocompatible film that forms the direct interface with the skin/tissue. As an example, a biocompatible double sided adhesive may be applied on the outer surface of the attachment unit to facilitate better contact of the probe and the subject's tissue.

The following are some specific non-limiting examples of a probe assembly, of probe parts, and of probe part configurations.

Figure 8:
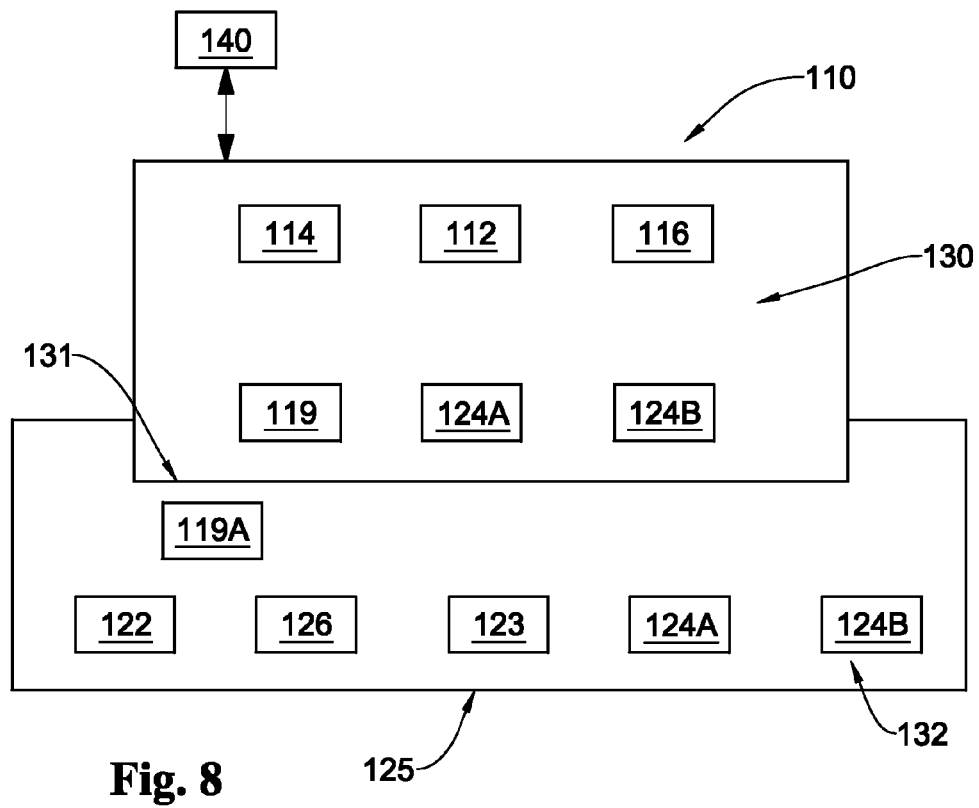
FIG. 8 is an example of the probe assembly of FIG. 1 being configured as a two-part device.

Reference is made to FIG. 8 showing a specific but non-limiting example of the configuration of the probe device of FIG. 1. The probe assembly 110 is configured as a two-part device comprising a probe body unit 130 and a probe-subject adhesive assembly unit 132 configured for interfacing between the probe assembly and the subject when the probe assembly is operating. The probe-subject adhesive assembly 132 is associated with a probe-subject adhesive media, e.g., comprises such a probe-subject adhesive media. The probe-subject adhesive assembly unit 132 may be configured so that it can be removed from, or connected to the probe body unit.

The probe body unit 130 includes at least the following components: the acoustic port 112, the light output port(s) 114, and the light input port(s) 116. The probe-subject adhesive assembly unit 132 interfaces an output surface of the probe body unit 131 through which acoustic and light radiations are transmitted in between the probe and the subject. Thus, when in operation, the probe assembly is brought into contact with the subject by the probe-subject adhesive assembly unit 132. A probe-subject adhesive assembly unit 132 is preferably constituted by an element configured to serve as a cover on the output surface 131 of the probe body unit 130 through which acoustic and light radiations are transmitted in between the probe body unit and the subject. The probe body contains an interface connector 119 that is connected to an interface connector on the probe-subject adhesive assembly unit 119A. The outer surface 125 of the probe-subject adhesive assembly unit includes an ultrasound-skin coupling pad 126 in the form of one of a selection of materials selected to provide the desired acoustic coupling between the acoustic port 112 and a subject. The probe-subject adhesive assembly unit 132 may include a coding chip 123. The probe-subject adhesive assembly unit 132 may comprise both flexible and rigid support materials.

Either one or all of the electronic unit 122, the coding chip 123, the sensor 124A, and the actuator 124B may be accommodated in the probe body unit or in the probe-subject adhesive assembly unit. With regard to the sensor 124A and actuator 124B system, it should be understood that its elements may be appropriately distributed between the probe body unit and the probe-subject adhesive assembly unit. In one embodiment, the probe-subject adhesive assembly unit 132 may be a disposable part of the probe device. In such an embodiment, the electronic memory unit 122 is preferably carried by the disposable probe-subject adhesive assembly unit 132, since it is aimed at recording and storing a subject's monitoring history.

Figure 9A:
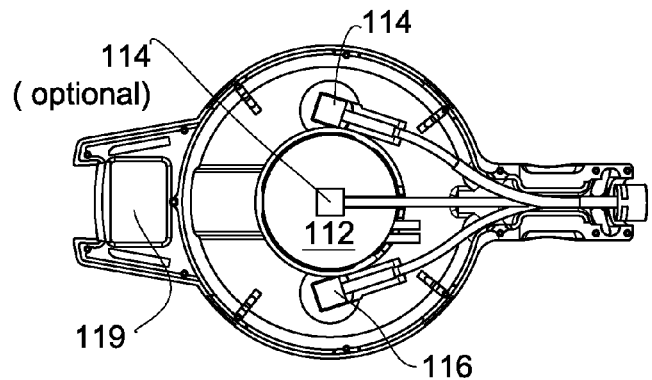
FIG. 9A exemplifies a specific configuration of a probe body suitable to be used in the present invention.
Figure 9B:
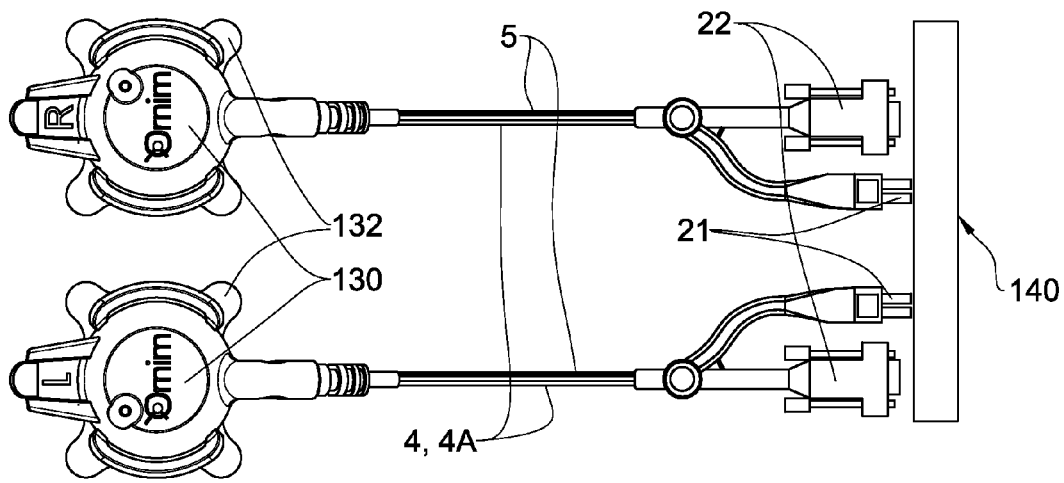
FIG. 9B exemplifies a system formed by two probe assemblies each having the probe body of FIG. 9A.
Figure 9C:
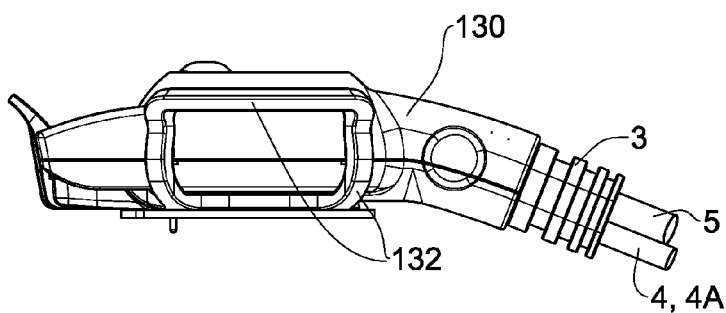
FIG. 9C shows an example of a two-part probe assembly.

It should be understood that in the case of a disposable (removable) probe subject-adhesive assembly unit 132, it may be used for multiple measurement sessions in which it is attached to the same or to different probe body units, as long is it is not removed from the subject's skin. When the adhesive assembly unit is attached to a probe body unit, the subject monitoring history data, stored in said disposable unit, is synchronized with the controller 140 connected to the respective probe body unit. However a disposable subject-adhesive assembly unit can serve as a memory utility holding the subject's monitoring history data even when the disposable unit cannot or is no longer used for further measurement sessions (e.g. in some embodiments, after the disposable subject-adhesive assembly unit had been detached from a subject skin it is not used in further measurements). Reference is made to FIGS. 9A-9C. In this embodiment, the probe assembly is configured as a two-part device comprising a probe body unit 130 and a probe-subject adhesive assembly unit 132 (shown in FIGS. 9B and 9C). The probe body 130 illustrated in FIG. 9A includes an acoustic transducer 112, two light output ports 114 (associated with light emitters), and a light input port 116 associated with a light detection unit. It should be noted that the provision of the second light output port is optional. Also provided in the probe body unit 130 is an interface connector 119 (an optional part of the sensor 124A actuator 124B system) configured to electronically connect the probe subject-adhesive assembly to the probe body unit and to carry out data/signal transmission between the probe body unit and the electronic memory unit (not shown here) in the probe-subject adhesive assembly unit (through the interface connector 119A of FIG. 8). A common housing 118 accommodates the elements of the probe body unit.

FIG. 9B illustrates a monitoring system which includes two probe assemblies each having the above-described probe body unit 130 and a probe-subject adhesive assembly unit 132 mounted on the probe body. Each probe is connected to an optical fiber bundle composed of two optical fibers for carrying electromagnetic radiation from the light source 4, and to the detector 4A. Each probe is connected to the controller 140 via an electrical cable 5 adapted for data/signal transmission and via an optical connector 21 and an electrical connector 22. The light source and the detection unit may be located in the controller 140.

FIG. 9C is a perspective side view of the above-described probe assembly with the probe-subject adhesive assembly 132 mounted onto the probe body 130. The probe is connected via a connector 3 including a strain relief, to an optical fiber bundle comprising two separate fibers 4 and 4A, which connect the probe assembly to the light source and to the detector (not shown here), respectively and also via an electric cable 5.

Figure 10A:
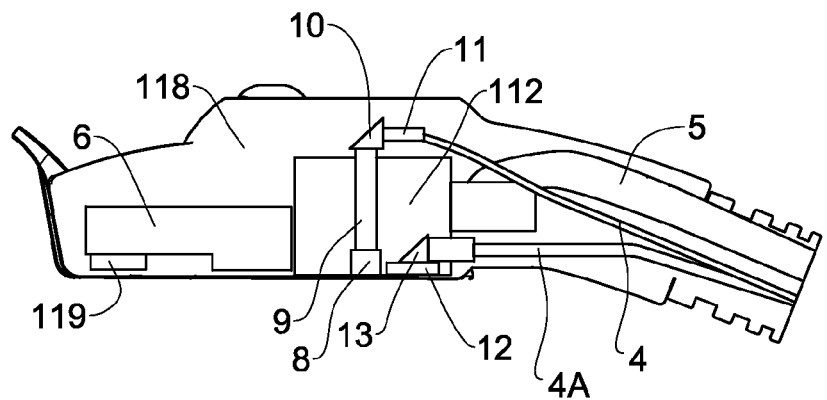
FIGS. 10A and 10B show two examples of the configuration of a probe body utilizing an off-probe photodetector via a light guide (A) or an on-probe photodetection system (B)
Figure 10B:
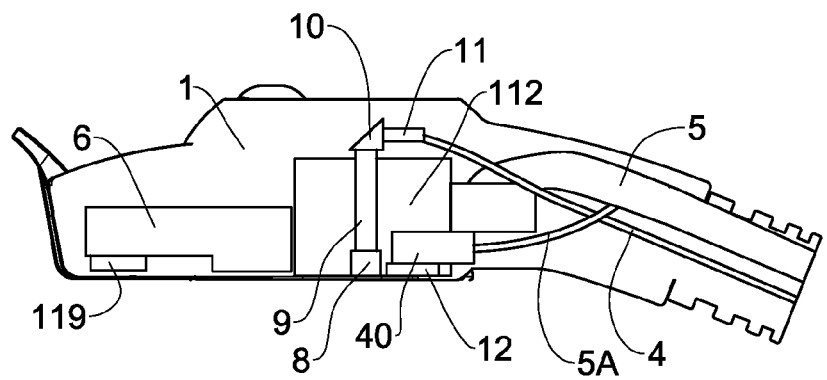

FIGS. 10A and 10B illustrate the internal architecture of the probe body unit 130 according to two embodiments. Each of the probe body units comprises an acoustic transducer 112 and an interface connector 119 for data/signal transmission to and from the electronic memory unit (e.g. in the probe-subject adhesive assembly unit) and to the interlock sensor/actuator when positioned on the probe-subject adhesive assembly unit. The probe body unit includes an electronic board 6 upon which the acoustic transducer, optical elements and the interface connector are assembled. Electronic board 6 includes an electronic circuit (e.g. PCB) connected to the acoustic transducer and to the electronic unit (e.g. in the probe-subject adhesive assembly unit) via the interface connector 119. Electronic board 6 is connected to the controller 140 (not shown) via an electric cable 5. Optionally, board 6 may be connected to the controller 140 via a wireless connection. The light output port 114 could be on the side of the acoustic port 112, as shown in FIG. 9A. Optionally, light output port 114 could be through the acoustic port 112 and may include an optical prism 10, an optical rod 9 and an optical window 8 for directing propagation of light from the optical fiber 4 (via connector 11) through the acoustic port 112. Optionally the light output port 114 could alternate between both options.

The examples of FIGS. 10A and 10B differ from one another in the type of light input port used (an off-probe photodetector in FIG. 10A and an on-probe photodetector (SPD) in FIG. 10B). In the example of FIG. 10A the light input port 116 serves only to transfer electromagnetic radiation collected from the subject's tissue to the photodetector in the controller 140. In this embodiment, the light input port 116 includes an optical window 12 and an optical prism 13 connected to an optical fiber 4A. Light collected from the tissue is directed by the prism and through the optical fiber to the monitoring system where it is further analyzed. In the example of FIG. 10B the light input port 116 is constituted by the detector itself (light sensitive chip 40) and thus serves to detect and measure the electromagnetic radiation collected from the subject's tissue, and to generate electric output indicative thereof. This electrical signal is then communicated to the monitor by means an electrical cable 5A.

Figure 11:
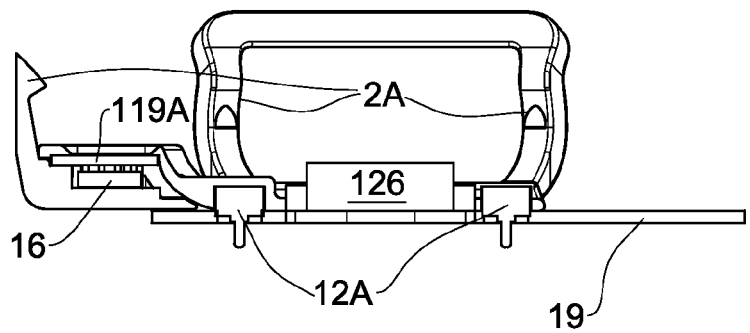
FIG. 11 exemplifies a configuration of a probe-subject adhesive assembly to be used with a probe body in the probe assembly of the present invention.
Figure 12:
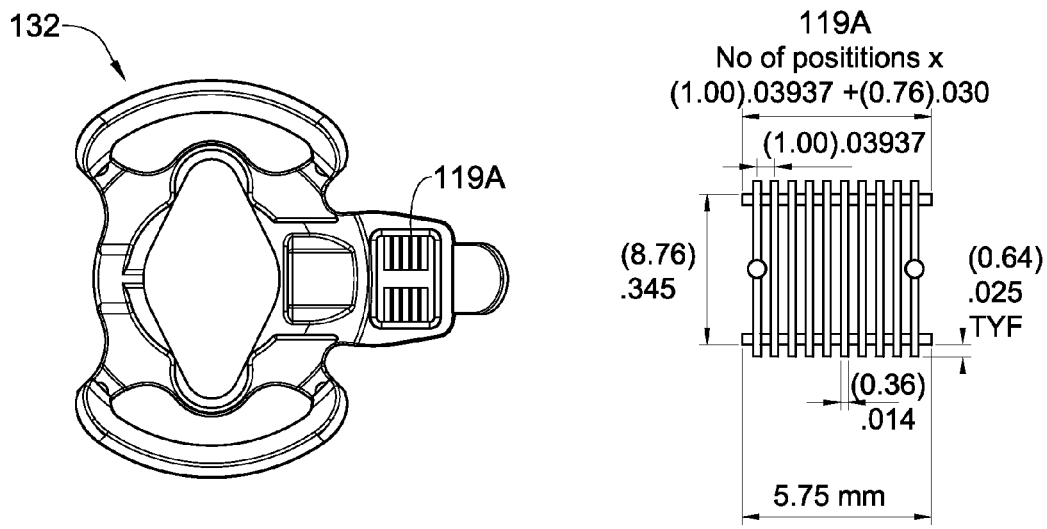
FIG. 12 provides a description of an interface connector that is used to connect the probe body to the probe-subject adhesive assembly.
Figure 13:
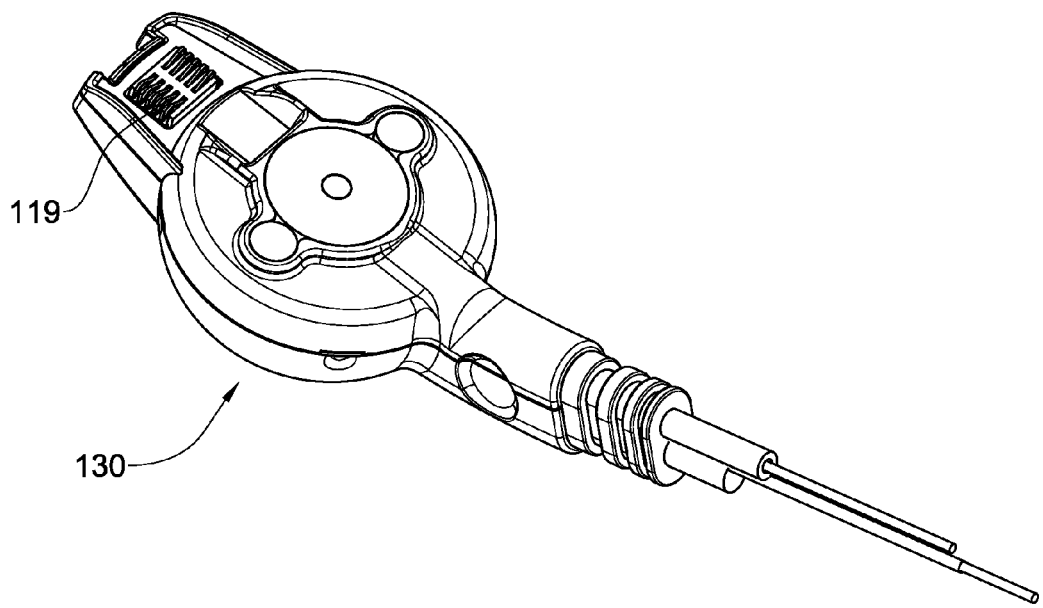
FIG. 13 shows the position of the interface connector on the probe body.

Reference is made to FIG. 11 illustrating an example of a probe-subject adhesive assembly unit 132 configured as a flexible cover on an output surface of the probe body unit (not shown). The probe-subject adhesive assembly can be attached onto a surface of the probe body by means of a snapping mechanism 2A. A part of the memory unit (122 of FIG. 1) and the coding chip (123 of FIG. 1) aimed at recording and storing the subject's monitoring history is embodied herein as a FLASH memory chip 16. The sensor and actuator system (124A and 124B of FIG. 1) includes at least one safety microswitch 12A (an option including two microswitches is shown in FIG. 11) configured to evaluate the attachment efficiency of the probe to the subject's tissue. The flash memory chip 16 and the safety microswitches 12A are connected to the electronic circuit of the control utility 120 via the interface connector 119A, which appears in FIG. 12. FIG. 12 shows the interface connector 119A, and its position on the probe-subject adhesive assembly unit. FIG. 13 shows the position of the interface connector 119 on the probe body, on electronic board 6 of FIG. 10. The outer surface of the probe-subject adhesive assembly, as described in FIG. 11, by which the probe assembly is brought into contact with the subject to be monitored, contains an ultrasound-skin coupling pad 126 configured to interface between the subject's tissue and the probe's acoustic port. A biocompatible double-sided adhesive 19 interfaces between the probe-subject adhesive assembly and the subject's skin.

The ultrasound transducer suitable to be used in the present invention may be a single element or may be formed by multiple acoustic transmitting elements. In case the transducer is made up of more than one element, each element may transmit ultrasound at a different phase shift as compared to the transmissions of the other elements.

Figure 14:
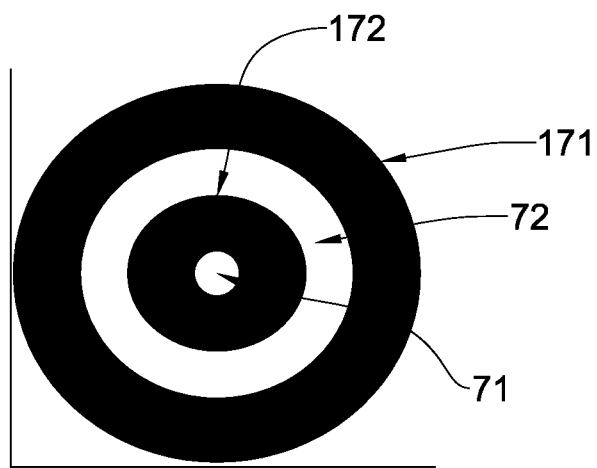
FIG. 14 shows an example of an acoustic transducer arrangement suitable to be used in the probe assembly of the present invention.

An example of an ultrasound transducer made up of two elements is illustrated schematically in FIG. 14. In this specific but non-limiting example there are two transducer rings, ring 172 having a smaller diameter than ring 171, and a spacing 72 in between. Each ring may transmit ultrasound waves at a different phase shift from the other ring. It should be noted that optical fibers for incoming and outgoing light from the tissue could pass outside the transducer elements, or they could pass through the transducer elements, or in between them. Considering the specific example of FIG. 14, the optical fibers could pass through the hole 71 within the small ring, or between the two rings 72, or outside the rings' area.

It should also be noted although not specifically shown, that the probe assembly may include multiple light input ports 116 and/or multiple light output ports 114. More than one light output port may be associated with the same light input port, namely the same light input port may be used for collecting light from the media illuminated by different light output ports, which are selectively operated to illuminate the media. These light output ports are located at different distances from the light input port and from the respective acoustic port, and thus detected light portions correspond to different regions of light-acoustic interactions in the media (e.g. different depths in the media). Likewise, more than one light input port maybe associated with one output port. For example, the acoustic transducer/port may have a ring-like shape, the first light output port is located inside the ring (e.g. at the center thereof), and the second light output port and the light input port are located outside the ring at opposite sides thereof. In reference to FIG. 14, if the transducer is made up of two elements, an output port can be inserted through the hole in small ring 71, and a set of input ports can be inserted between the rings 72.

While this invention has been particularly shown and described with references to preferred embodiments thereof, it will be understood by those skilled in the art that various changes in form and details may be made therein without departing from the scope of the invention encompassed by the appended claims.

What is claimed is:

1. A probe assembly for use in monitoring one or more parameters of a subject, the probe assembly comprising:
    an acoustic port for transmitting acoustic radiation into a region of interest in the subject,
    at least one light output port for transmitting incident light towards the region of interest, at least one light input port for receiving light returned from the subject; and a control utility, wherein said control utility is integrated in the probe assembly and is configured for automatically controlling a monitoring procedure so as to start the monitoring procedure upon identifying that at least one predetermined condition of the monitoring procedure is satisfied and to stop the monitoring procedure upon identifying that at least one predetermined condition of the monitoring procedure is not satisfied, said control utility comprising at least one of the following:

(i) a coding chip adapted for communication with an external controller, the coding chip being adapted for generating an activation code to be identified by the external controller, such that identification of the activation code generated by the coding chip of the probe assembly is a condition to allow operation of said probe assembly, and (ii) a safety system comprising a sensor configured for sensing whether at least one safety condition of the monitoring procedure is satisfied, and an actuator configured to enable or disable the monitoring procedure in response to a sensing indication produced by said sensor depending on said at least one safety condition.

2. The probe assembly of claim 1, wherein the control utility further comprises a memory unit adapted for recording data indicative of measurements taken on a specific subject during a certain period of time, thereby enabling use of said data as a measurement history of the specific subject, the measurements being taken by one or more of the probe assemblies.

3. The probe of claim 1, wherein the sensing system is adapted for sensing a degree of attachment between the probe assembly and the subject, said degree of attachment being indicative of the at least one safety condition relating to the degree of coupling between the subject and at least one of said acoustic and light ports.

4. The probe assembly of claim 1, being configured as a two-part device comprising a first probe body unit and a second unit, wherein said second unit interfaces with the subject when the probe assembly is put in operation.

5. The probe assembly of claim 4, wherein the first probe body unit and the second unit are configured such that the second unit is attachable to and detachable from the first probe body unit.

6. The probe assembly of claim 5, wherein said second unit carries at least a part of the control utility.

7. The probe assembly of claim 6, wherein said second unit carries a memory unit, the memory unit being adapted for recording data indicative of measurements taken on a specific subject during a certain period of time, enabling use of said data as a measurement history of the specific subject, the measurements being taken by one or more of the probe assemblies.

8. The probe assembly of claim 4, wherein the second unit comprises an adhesive media.

9. The probe assembly of claim 4, wherein the first probe body unit comprises the acoustic port, the at least one light output port, and the at least one light input port.

10. The probe assembly of claim 4, wherein the second unit interfaces an output surface of the first unit through which acoustic and light radiations are transmitted in between the probe assembly and the subject.

11. The probe assembly of claim 8, wherein the second unit interfaces an output surface of the first unit and transmits acoustic and light radiation therethrough towards and from the subject.

12. The probe assembly of claim 11, wherein said second unit is configured as a flexible cover on an output surface of the first unit.

13. The probe assembly of claim 8, wherein said adhesive media comprises an ultrasound-skin coupling pad comprising one or more materials selected to provide desired acoustic coupling between the acoustic port and the subject and being substantially transparent for a wavelength range used in the probe.

14. The probe assembly of claim 1, further comprising an ultrasound-skin coupling pad comprising one or more materials selected to provide desired acoustic coupling between the acoustic port and the subject.

15. The probe assembly of claim 14, wherein said ultrasound-skin coupling pad is substantially transparent to light of a predetermined wavelength range.

16. The probe assembly of claim 14, wherein said ultrasound-skin coupling pad has acoustic impedance similar to that of tissue or skin of the subject.

17. The probe assembly of claim 14, wherein said ultrasound-skin coupling pad has a matrix that is a polymerization product of a suspension of elastomeric resin in a plasticizer.

18. The probe assembly of claim 14, wherein said ultrasound-skin coupling pad is electrically insulating.

19. A probe assembly for use in monitoring one or more parameters of a subject, the probe assembly being configured as a two-part device comprising first and second units, wherein:

the first unit is configured as a probe body unit and comprises an acoustic port for transmitting acoustic radiation into a region of interest in the subject, at least one light output port for transmitting incident light towards the region of interest, at least one light input port for receiving light returned from the subject, the second unit comprises an adhesive assembly interfaces with the subject when the probe assembly is put in operation, the second unit is attachable to and detachable from the first unit and comprises an electronic unit having a memory utility adapted for recording data indicative of measurements taken on a specific subject during a certain period of time, enabling use of said data as a measurement history of the specific subject, the recorded data corresponding to the measurements being taken by one or more of the probe assemblies.

20. The probe assembly of claim 19, further comprising at least one of the following: (i) a coding chip configured to generate an activation code that allows operation of said probe assembly; and (ii) a sensing system comprising a sensor configured for sensing and determining a degree of coupling between the subject and at least one of said acoustic and light ports and an actuator for selectively enabling and disabling the monitor procedure depending on the determined degree of coupling.

21. The probe assembly of claim 20, wherein at least one of said coding chip and said sensing system is at least partially located in the first unit.

22. A monitoring system for monitoring one or more parameters of a subject, the monitoring system comprising:

at least one probe assembly, the probe assembly comprising: an acoustic port for transmitting acoustic radiation into a region of interest in the subject, at least one light output port for transmitting incident light towards the region of interest, at least one light input port for receiving light returned from the subject, and a control utility integrated in the probe assembly and, a controller which is external to said at least one probe assembly and is in communication with the control utility integrated in the probe assembly;

wherein said control utility is configured and operable to carry out at least one of the following: (i) recording data indicative of measurements taken on the specific subject during a certain period of time; (ii) communicating with the external controller using generation of an activation code enabling said controller to identify the probe assembly such that identification of the activation code is a condition to allow operation of said at least one probe assembly; and (iii) sensing at least a degree of attachment between the probe assembly and the subject and enabling operation of the probe assembly upon identifying that said degree of attachment satisfies a predetermined safety condition.

23. The system of claim 22, comprising at least two of the probe assemblies.

24. The system of claim 23, wherein the control utility of each of the at least two probe assemblies is adapted for storing data indicative of results of measurements taken by all the probe assemblies.

25. The probe assembly of claim 1, wherein said safety system is configured and operable for controlling the at least one condition of the monitoring procedure, said at least one condition comprising at least one of the following: existence of a contact between the probe assembly and the subject; a degree of coupling between the subject and at least one of said acoustic and light ports; and positioning of the probe assembly in a docking station.

* * * * *

UNITED STATES PATENT AND TRADEMARK OFFICE
CERTIFICATE OF CORRECTION

PATENT NO. : 9,078,617 B2  
APPLICATION NO. : 12/402582  
DATED : July 14, 2015  
INVENTOR(S) : Ofer Pintel et al.

Page 1 of 1

It is certified that error appears in the above-identified patent and that said Letters Patent is hereby corrected as shown below:

In The Claims

At claim 19, column 16, line 39, insert --and-- after "adhesive assembly".

Signed and Sealed this  
Fifteenth Day of March, 2016

Michelle K. Lee  
*Director of the United States Patent and Trademark Office*